(12) United States Patent
Leledy et al.

(10) Patent No.: US 10,281,311 B2
(45) Date of Patent: May 7, 2019

(54) METHOD OF OPERATING A LIQUID-LEVEL TRANSMITTER DEVICE AND IMPLEMENTATION THEREOF

(71) Applicant: Dresser, Inc., Addison, TX (US)

(72) Inventors: Stephane Marcel Leledy, Courbevoie (FR); Denis Auguste Vital, Montsecret (FR)

(73) Assignee: Dresser, LLC, Addison, TX (US)

( * ) Notice: Subject to any disclaimer, the term of this patent is extended or adjusted under 35 U.S.C. 154(b) by 1100 days.

(21) Appl. No.: 14/484,037

(22) Filed: Sep. 11, 2014

(65) Prior Publication Data

US 2016/0076929 A1   Mar. 17, 2016

(51) Int. Cl.
*G01F 23/24* (2006.01)
*G01F 23/34* (2006.01)

(52) U.S. Cl.
CPC ............ *G01F 23/246* (2013.01); *G01F 23/34* (2013.01)

(58) Field of Classification Search
None
See application file for complete search history.

(56) References Cited

U.S. PATENT DOCUMENTS

| | | | |
|---|---|---|---|
| 3,498,090 A * | 3/1970 | Mason | D06F 39/087 137/387 |
| 3,782,205 A * | 1/1974 | Fletcher | G01C 19/04 73/497 |
| 4,019,363 A * | 4/1977 | Sanford | G01D 18/00 73/1.73 |
| 4,026,145 A | 5/1977 | Nagy et al. | |
| 4,037,598 A * | 7/1977 | Georgi | A61M 5/1689 128/DIG. 12 |
| 4,250,853 A | 2/1981 | Ninomiya | |
| 4,481,655 A | 11/1984 | Annis et al. | |
| 4,803,885 A * | 2/1989 | Nonomura | G01L 3/102 73/862.333 |
| 5,440,883 A | 8/1995 | Harada | |
| 5,656,779 A * | 8/1997 | Bronowicki | B06B 1/0261 536/24.3 |
| 6,439,066 B1 * | 8/2002 | Norton | G01L 3/102 73/862.333 |
| 6,473,708 B1 * | 10/2002 | Watkins | G01K 15/00 219/497 |
| 7,181,980 B2 | 2/2007 | Wium | |
| 7,208,706 B2 | 4/2007 | Haimer et al. | |
| 7,322,250 B1 * | 1/2008 | Discenzo | G01L 1/241 73/800 |
| 7,392,714 B2 * | 7/2008 | Maguire | G01L 3/1485 192/105 A |
| 7,673,377 B2 | 3/2010 | Clew | |

(Continued)

OTHER PUBLICATIONS

Technical specification, Masonellian Products, 12400 Series Digital Level Transmitter (2012).

*Primary Examiner* — Janet L Suglo
*Assistant Examiner* — Leonard S Liang
(74) *Attorney, Agent, or Firm* — Paul Frank + Collins P.C.

(57) ABSTRACT

A method that configures a liquid-level transmitter device to generate a measured value for a level of a liquid. The method includes steps to correct for changes in physical properties of one or more components of the device. In one embodiment, the method utilizes a correction value that incorporates data from a temperature sensor disposed inside of the device, for example, inside of the electronics member.

10 Claims, 5 Drawing Sheets

(56) References Cited

U.S. PATENT DOCUMENTS

| | | | |
|---|---|---|---|
| 7,908,727 B2 | 3/2011 | Clew | |
| 8,197,133 B2* | 6/2012 | Schultz | G01F 1/6965 374/1 |
| 8,533,951 B2 | 9/2013 | Nava et al. | |
| 9,711,038 B1* | 7/2017 | Pennebaker, III | G08C 17/02 |
| 2003/0041664 A1* | 3/2003 | Ariyoshi | G01F 1/6986 73/204.26 |
| 2004/0144178 A1* | 7/2004 | Ohmi | G01D 3/022 73/708 |
| 2007/0199389 A1* | 8/2007 | Tombs | G01F 1/8436 73/861.357 |
| 2009/0132185 A1* | 5/2009 | Furuse | G01M 3/3263 702/51 |
| 2009/0293625 A1* | 12/2009 | Sundet | G01L 9/125 73/708 |
| 2010/0101105 A1* | 4/2010 | Hon | B23Q 17/20 33/503 |
| 2010/0107886 A1* | 5/2010 | Xiao | D06F 75/12 99/281 |
| 2010/0224011 A1* | 9/2010 | Klimenko | B62D 6/10 73/862.326 |
| 2010/0301923 A1* | 12/2010 | Anderson | G01R 31/2849 327/513 |
| 2010/0312514 A1* | 12/2010 | Bonato | G01D 3/022 702/104 |
| 2012/0226449 A1* | 9/2012 | Delache | G01F 1/36 702/45 |
| 2013/0081480 A1* | 4/2013 | Giovanoni | G01F 1/62 73/862.333 |
| 2013/0291657 A1* | 11/2013 | Purekar | G01L 3/101 73/862.333 |
| 2016/0033340 A1* | 2/2016 | Todd | G01K 15/005 374/1 |

\* cited by examiner

METHOD OF OPERATING A LIQUID-LEVEL TRANSMITTER DEVICE AND IMPLEMENTATION THEREOF

BACKGROUND

The subject matter disclosed herein relates to improvements in flow monitoring technology for use in industrial processes, with particular discussion about embodiments of a liquid-level transmitter device that integrates with control systems for the industrial processes, the embodiments being configured to compensate for changes in operative characteristics of the device to generate measured values for liquid levels in a reservoir.

Level transmitters and like devices are useful to monitor liquid levels in a process line. These devices have particular utility to industrial processes typical of chemical, petrochemical, oil & gas extraction and transportation, and the like. In one form, the devices can have a structure to convert buoyant action of one or more components into a measured value that reflects the level of liquid in a vessel or a reservoir. The structure can also communicate this measurement to a process control system that regulates operation of devices on the process line.

The structure can incorporate various components that operate to convey the buoyant action as torque (or torsion or rotation). These components can include shafts (and like tubular, elongate elements) that couple the buoyant component with a sensor and/or other element that generates the measurement. In one example, the shaft can rotate in response to the torque. The sensor can register the rotation of the shaft, effectively generating a value for the measured value that is proportional to the displacement of the buoyant component.

Unfortunately, accuracy of this value depends in large part on the operative characteristics of the structure. Because the structure is largely mechanical, small changes in physical properties, dimensions, and tolerances can frustrate the proportionality that the structure relies upon to generate accurate information about the level of liquid. Many of these changes relate to one or more operating temperatures (e.g., ambient or environment temperature, process temperature, device temperature, etc.). Nevertheless, these problems can permeate throughout the structure and, ultimately, induce errors in the value of the measurement.

Conventional devices employ several solutions to address issues of accuracy that arise in connection with the operative characteristics of level transmitter devices. In many cases, the solution relies upon manual entry of data to "artificially" rectify the error in the value of the measurement. This data may define temperature (e.g., process temperature) and/or other operating parameters (e.g., specific gravity, calibration parameters, etc.). The data may also include values for coefficients that algorithms use to compensate for changes that occur in the operative characteristics of the device. In other conventional devices, the data may include measurements, namely, temperature measurements from sensors disposed external, or outside of, the level transmitter device.

However, none of these solutions address accuracy issues across a broad swath of applications. Implementations that position the level transmitter device in hazardous areas, for example, can introduce conditions that distort measurements from external sensors and/or foreclose individuals from access to the level transmitter device. Moreover, data entry by individuals may exacerbate problems, particularly if the individual introduces inaccurate information that is meant to correct the error in the value of the measurement.

BRIEF DESCRIPTION OF THE INVENTION

This disclosure introduces a solution that allows liquid-level transmitter devices to automatically compensate for changes in the operative characteristics that can skew the values for measurements that reflect the level of liquid. This solution does not, however, require embodiments of the liquid-level transmitter device to interface with external sensors or require extensive data entry; instead the embodiments can be configured to process data from existing sensors, often found inside of components of the level transmitter device. These embodiments also forgo the need for manual data entry in lieu of pre-defined data (e.g., data tables) that can significantly reduce quality and error problems more typical of conventional solutions and designs for liquid-level transmitter devices.

BRIEF DESCRIPTION OF THE DRAWINGS

Reference is now made briefly to the accompanying drawings, in which.

Where applicable like reference characters designate identical or corresponding components and units throughout the several views, which are not to scale unless otherwise indicated.

DETAILED DESCRIPTION

The discussion below describes implementations of a liquid-level transmitter device ("transmitter device") for use to monitor levels of a liquid in vessels (e.g., pipes, tanks, reservoirs, etc.) in an industrial process line. At a high level, the transmitter device has a buoyant member that moves in response to changes in the level of the liquid in the vessel. The transmitter device can translate the movement into a measured value that reflects the level of the liquid. As noted more below, liquid-level transmitter devices made in accordance with this disclosure offer built-in compensation to improve the accuracy of the measured value. This feature addresses changes in operative characteristics of one or more components on the liquid-level transmitter device. Of particular interest, it has been found that on some conventional devices, even a small drift in Young's Modulus (~0.0285%/° C.) can lead to errors in the measured value that reflects the level of the liquid. These findings indicate that such drift has more significance in applications with liquids that have relatively small specific gravity. The embodiments herein, however, can automatically compensate for drift in Young's Modulus to resolve potential errors in the values for the measured value.

Figure 1:
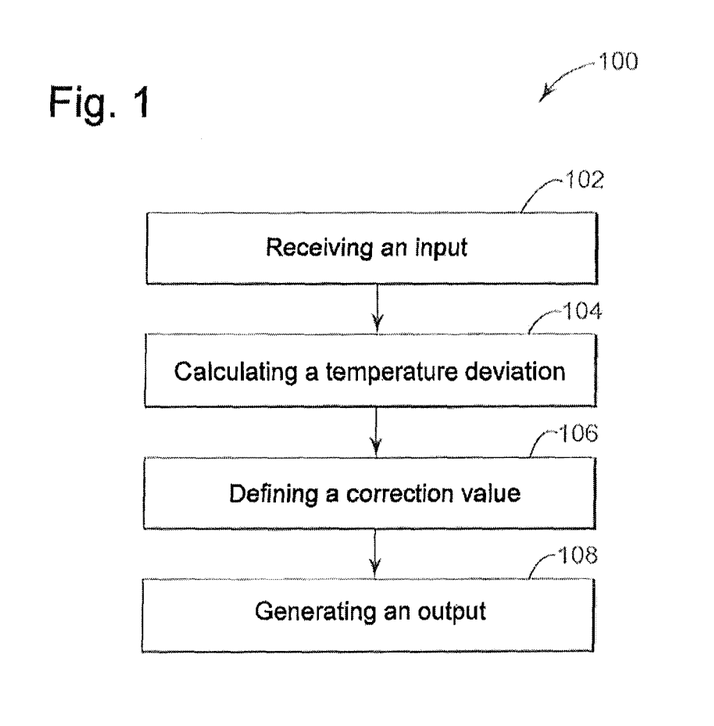
FIG. 1 depicts a flow diagram of an exemplary embodiment of a method for compensating for changes in operative characteristics of a level transmitter device.

FIG. 1 depicts a flow diagram of an exemplary embodiment of a method 100 for generating a measured value on a liquid-level transmitter device. The method 100 includes, at step 102, receiving an input defining a first input temperature. The method 100 also includes, at step 104, calculating a temperature deviation between the first input temperature and a second input temperature that originates from a sensor member disposed on the liquid-level transmitter device. In one example, the second input temperature relates to data that originates during calibration of the liquid-level transmitter device. The method 100 also includes, at step 106, defining a correction value using the temperature deviation and a drift value describing a physical property of a component on the liquid-level transmitter device. The method 100 further includes, at step 108, generating an output defining a measured value that includes the correction value.

Figure 2:
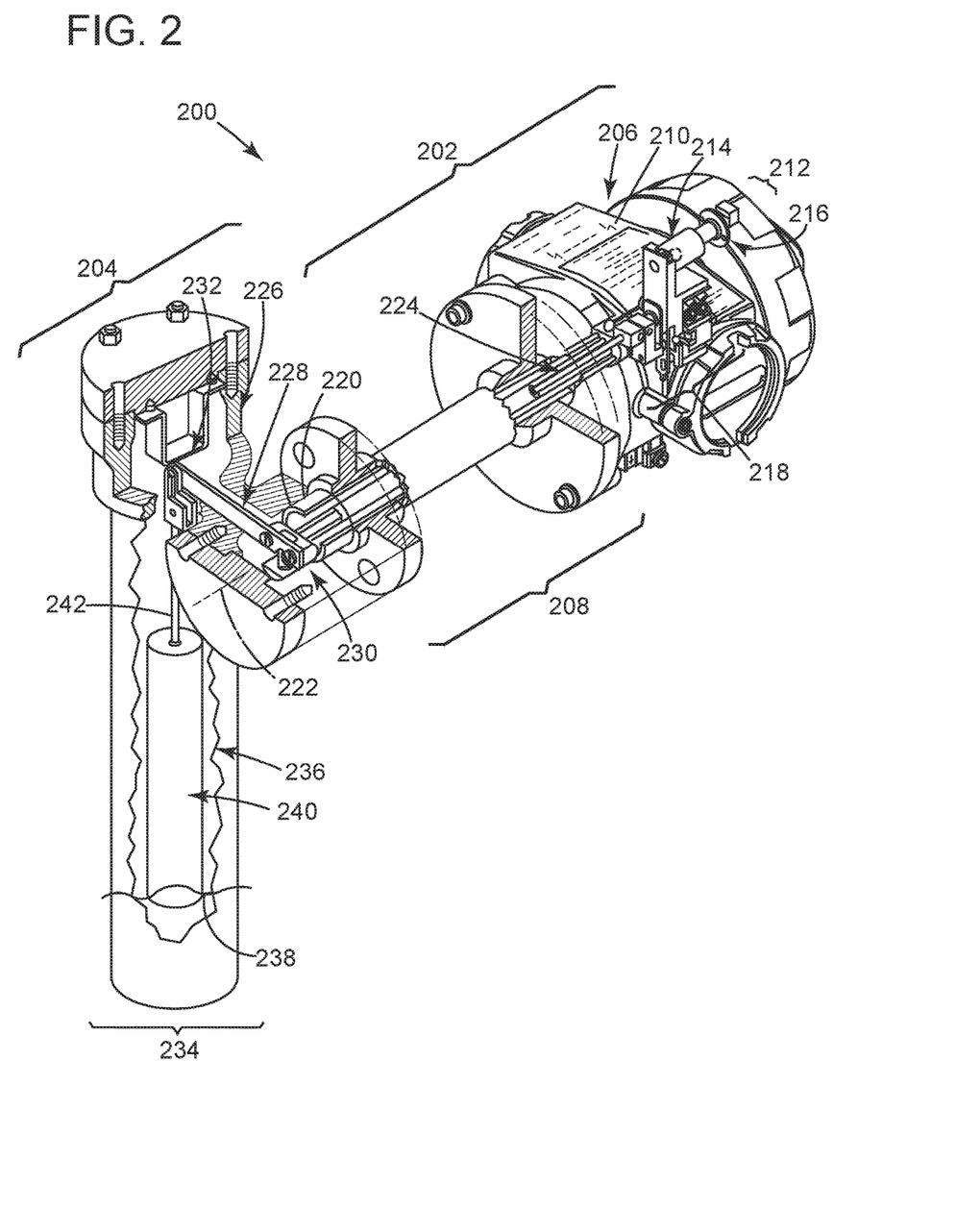
FIG. 2 depicts a perspective view of an exemplary embodiment of a liquid-level transmitter device.

The method 100 offers built-in compensation to reduce errors that might occur in the measured value on the liquid-level measurement device. FIG. 2 depicts a perspective view of an exemplary embodiment of a liquid-level transmitter device 200 (also, "device 200"). This embodiment has an instrument component 202 that couples with a measurement component 204. For clarity, the instrument component 202 is shown generally in solid lines; however, as indicated more below, the instrument component 202 may be constructed so as to obscure some parts from view. Moving from right to left in the diagram of FIG. 2, the instrument component 202 can include an electronics member 206 and a torque tube assembly 208. The electronics member 206 has a housing 210 that encloses a sensor member 212, shown here with a target element 214 and a sensor element 216. The sensor member 212 can also include an intermediary motive member 218 that couples the target element 214 with the torque tube assembly 208. This configuration facilitates movement of the target element 214 relative to the sensor element 216.

As also shown in FIG. 2, the torque tube assembly 208 can include a torque tube member 220 with a longitudinal axis 222. The torque tube member 220 couples with the intermediary motive member 218 at one end via, for example, a rod member 224. At the other end, the torque tube member 220 can couple with the measurement component 204. This combination can generate motive action of the target member 214. In one example, the measurement component 204 includes a torque generating assembly 226 with a torque arm 228 having a first end 230 and a second end 232. The first end 230 couples with the torque tube assembly 208, with one construction of the torque arm 228 securing with the torque tube member 220. The second end 232 couples with a displacement assembly 234 that is disposed in a reservoir 236 that is configured to hold a liquid 238. The displacement assembly 234 has a displacer member 240 and an extension arm 242 that couples the displacer member 240 with the torque arm 228. The displacer member 240 is configured for buoyant movement in response to changes in the level of the liquid 238.

The level transmitter device 200 can monitor the level of the liquid 238 inside of the reservoir 236. During operation, movement of the displacer member 240 acts on the torque arm 228 to generate a force, e.g., torque, on the torque tube member 220 about the longitudinal axis 222. This force will increase and decrease by an amount directly proportional to the change in the level of the liquid 238. In one implementation, the torque causes the torque tube member 220 to rotate about the longitudinal axis 222 from a first radial orientation to a second radial orientation. The intermediary motive member 218 transfers this radial orientation to the target element 214. In one example, the intermediary motive member 218 sets a position for the target element 214 relative to the sensor element 216. In turn, the sensor element 216 generates a signal in response to the position of the target element 214. This signal corresponds with the measured value for the level of the liquid 238 in the reservoir 236.

Changes in the torque tube member 220 can induce errors in the relationship between the displacement of the displacer member 240 and the position of the target element 214. The method 100 takes into consideration the physical properties that are responsible for these errors. For example, changes in material properties (e.g., Young's Modulus) can affect the stiffness of the torque tube member 220. These changes can cause deviations in the radial orientation as relates to the actual displacement of the displacer member 240. As noted more below, the method 100 corrects for these deviations to improve the accuracy of the measured value of the device 200.

Referring also to FIG. 1, the step of receiving the input (e.g., at step 102) can identify an operating mode for the device 200 to generate the measured value. The operating mode may include a first mode (also "a process mode") that uses a process temperature to compensate for drift in the physical properties (e.g., Young's Modulus). Examples of the process temperature can reflect the temperature of the fluid in the process line (e.g., in a range of about −210° C. to about 450° C.), although this disclosure also contemplates other process-related temperatures (e.g., environment) that might be useful to compensate for changes in operating characteristics of the device 200. In other configurations, the operating mode may include a second mode (also "a temperature mode") that uses an operating temperature from the device 200. This operating temperature may fall in a range of from about −50° C. to about 85° C. In one embodiment, the operating temperature describes the temperature inside of the housing 210 of the electronics member 206 to compensate for drift in the Young's Modulus of the torque tube member 220.

Figure 3:
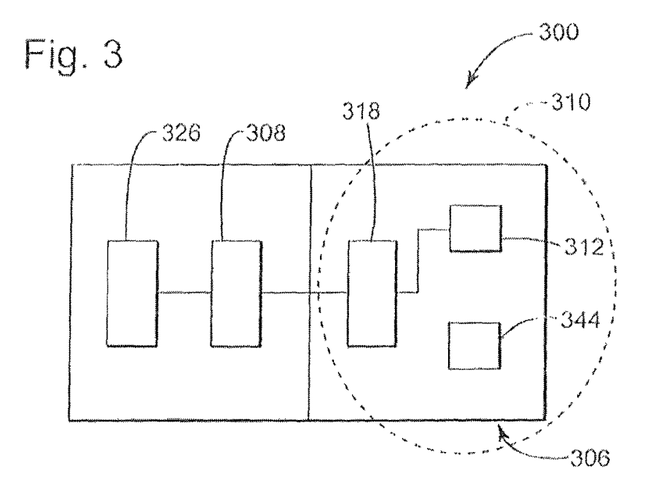
FIG. 3 depicts a schematic diagram of an exemplary embodiment of a liquid-level transmitter device.

The step of calculating the temperature deviation (e.g., at step 104) is useful for compensating for errors that occur due to drift in Young's Modulus. FIG. 3 illustrates a schematic diagram of an exemplary embodiment of a liquid-level transmitter device 300. This schematic diagram shows, at a high-level, the relationship between the torque tube assembly 308, the intermediary motive member 318, and the torque generating assembly 326. As also shown in FIG. 3, the electronics member 306 can include the first sensor member 312 and a second sensor member 344. Examples of the second sensor member 344 can include a thermistor, a thermocouple, digital sensor, and/or like devices that are sensitive to changes in temperature. The second sensor member 344 can reside inside of the housing 310. In one configuration, the sensor members 312, 344 reside on the same substrate (e.g., a printed circuit board) and/or are part of the same electronic component that is disposed in the electronics member 306.

During operation, the second sensor member 344 generates a signal that reflects the operating temperature inside of the electronics member 306. In temperature mode, the first input temperature may reflect this operating temperature. The second input temperature may reflect a calibration value for the second sensor member 344. The method 100 may use the calibration value in both the temperature mode and the process mode. Examples of the calibration value correspond with temperature data that results from a calibration procedure, typically performed on the liquid-level transmitter device 300 off-line and/or outside the working environment. The calibration value may comprise a low value and a high value, each being calculated from a series of readings from the first sensor member 312. In one embodiment, the temperature deviation can be calculate according to Equation (1) below, $$\Delta_t = T_1 - T_2, \qquad \text{Equation (1)}$$

wherein $\Delta_t$ is the temperature deviation, $T_1$ is the first input temperature, and $T_2$ is the second input temperature.

As also shown in FIG. 1, the step of defining a correction value (e.g., at step 106) can use the temperature deviation (e.g., $\Delta_t$) to compensate for errors in the measured value. Examples of the drift value may quantify the change in one or more physical properties that necessitate the requisite correction in the measured value. For Young's Modulus, the drift values may identify a percent change (%) in a value for Young's Modulus relative to temperature (° C.), i.e., (%/° C.). These drift values may comprise a single value or multiple values. The single value may be configured to identify the drift value for a wide array of materials (e.g., an average drift value). On the other hand, multiple values may be used that identify the drift value for each individual or group of materials. In one embodiment, these multiple values may reside in a data table as shown in the example of Table 1 below:

TABLE 1

| Identifier (I) | Material (M) | Drift Value (d$_v$) |
| --- | --- | --- |
| 1 | M1 | DV1 |
| 2 | M2 | DV2 |
| 3 | M3 | DV3 |
| 4 | M4 | DV4 |
| 5 | M5 | DV5 |

The method 100 can retrieve data from the data table (e.g., Table 1) to generate the output, as desired. As shown above, the drift values can be arranged according to material (M), with each material (M) having a drift value (DV) associated therewith. The identifier (I) may associate with the material (M). This feature can provide the method 100 with the location in the data table for the material (M) that corresponds with the composition of the torque tube member (e.g., torque tube member 220 of FIG. 2). In one implementation, the identifier (I) can operate as a pre-defined variable that the method 100 can access and/or as data that an end user enters, e.g., into an interface and/or other operative means.

The correction value may incorporate the drift value (from the data table) and the temperature deviation. In one embodiment, the correction value can comprise a first correction value and a second correction value, which are different from one another. Each include a drift component having a value calculated in accordance with Equation (2) below, $$D = \frac{d_v * \Delta_t}{100}, \qquad \text{Equation (2)}$$

wherein D is the drift component, $d_v$ is the drift value, and $\Delta_t$ is the temperature deviation. The first correction value can use the drift component, as shown in the example of Equation (3) below, $$CV_1 = 1 - D, \qquad \text{Equation (3)}$$

wherein $CV_1$ is the first correction value. The second correction value can also use the drift component and, moreover, can include one or more specific gravity components (e.g., a first specific gravity component and a second specific gravity component) as shown in Equations (4) below, $$CV_2 = D \times SG_{max} \times SG_{ratio}, \qquad \text{Equation (4)}$$

wherein $CV_2$ is the second correction value, D is the drift component, $SG_{max}$ is the maximum specific gravity allowed for the displacer member (e.g., displacer member 240 of FIG. 2), and $SG_{ratio}$ is a ratio of specific gravity. Values for $SG_{max}$ may be determined in accordance with Equation (5) below, $$SG_{max} = \frac{DW}{DV}, \qquad \text{Equation (5)}$$

wherein DW is the weight of the displacer member (e.g., displacer member 240 of FIG. 2) and DV is the volume of the displacer member (e.g., displacer member 240 of FIG. 2). In one example, values for $SG_{ratio}$ depend on the application of the liquid-level transmitter to monitor a level or to monitor an interface (between two liquids). These values can be determined in accordance with one or more of Equations (6) and (7) below, $$SG_{ratio1} = \frac{1}{SG_{ser}}, \qquad \text{Equation (6)}$$

$$SG_{ratio2} = \frac{1}{SG_{Highser} - SG_{Lowser}}, \qquad \text{Equation (7)}$$

$SG_{ratio}$ is a first ratio for a level application, $SG_{ser}$ is the specific gravity of service for the level application, $SG_{ratio2}$ is a second ratio for an interface application, $SG_{Highser}$ is the high bound (or value) for the specific gravity of service for the interface application, and SGLowser is the lower bound (or value) for the specific gravity of service for the interface application.

The step of generating the output (e.g., at step 108) uses the correction value to provide the measured value that takes into consideration drift in Young's Modulus. The output can comprise different values for the measured value that correspond with different modalities of calculation, different selections of data, and/or different data sampling. In one embodiment, the output comprises a normalized value for the measured value that can be calculated in accordance with Equation (8) below, $$L_N = (CV_1 \times M_N CV_2) \qquad \text{Equation (8)}$$

wherein $L_N$ is the normalized value, $CV_1$ is the first correction value, $CV_2$ is the second correction value, and $M_N$ is the measured displacement (normalized between 0 and 1) from the first sensor member. In other embodiments, the output comprises a current value for the measured value that can be calculated in accordance with Equation (9) and (10) below, $$L_C = (CV_1 \times M_N + CV_3), \qquad \text{Equation (9)}$$

$$CV_3 = M_{LZero} \times (CV_1 - 1) - (M_{LSpan} - M_{LZero}) \times CV_2, \qquad \text{Equation (10)}$$

wherein $L_C$ is the current value, $CV_1$ is the first correction value, $CV_2$ is the second correction value, $CV_3$ is a third correction value, $M_{LZero}$ is the low value for the measured displacement recorded from the first sensor during calibration, and $M_{LSpan}$ is the high value for the measured displacement recorded from the first sensor during calibration.

Figure 4:
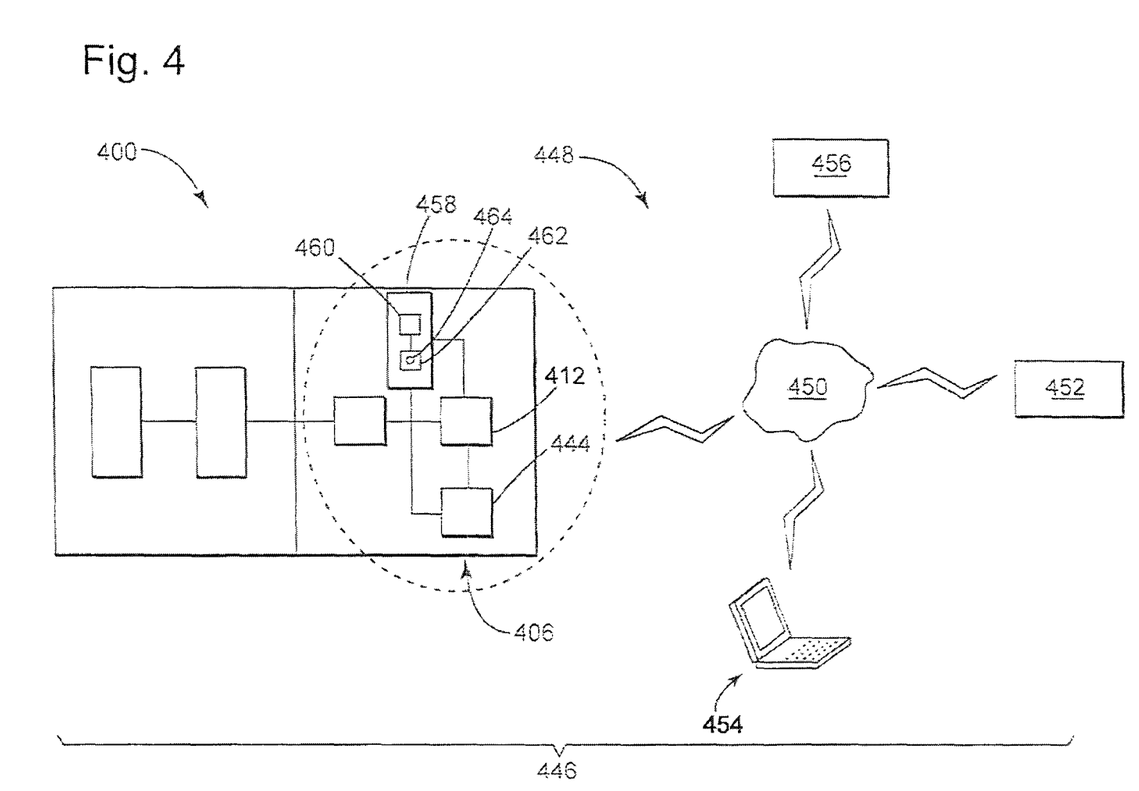
FIG. 4 depicts a schematic diagram of an exemplary embodiment of a liquid-level transmitter device as part of a process control system.

FIG. 4 depicts a schematic diagram of an exemplary embodiment of a liquid-level transmitter device 400. This example is part of a process control system 446 that is configured to operate one or more devices (e.g., valves) found on a process line. The electronics member 406 couples with a network system 448 via a network 450 that can transfer data, information, and signals by way of wired protocols (e.g., 4-20 mA, Foundation Fieldbus, etc.) and/or wireless protocols, many of which find use in a plant or factory automation environment. The network 450 facilitates communication between the electronics member 406, a process control server 452, a terminal 454, and/or an external server 456. Examples of the terminal 454 can include computers (e.g., laptops, desktops, etc.) as well various computing devices (e.g., smartphones, tablets, etc.). The electronics member 406 can include a processing member 458. The processing member 458 can have one or more processors (e.g., a first processor 460) that can access one or more memory (e.g., a first memory 462), shown here on-board the processing member 458 with the first processor 460. The memory 462 may include executable instructions 464 in the form of instructions (e.g., software, firmware, etc.) that the processor 460 is configured to execute to instruct operation of the level transmitter device 400, At a high level, the processing member 458 can be configured to generate the measured value. This configuration may operate to execute the steps of the method 100 (FIG. 1), which can be coded as one or more of the executable instructions 464. Examples of the executable instructions 464 can embody software, firmware, and like computer-implemented programs and methodology. While shown stored on the first memory 462 in the present example, this disclosure does contemplate implementations in which executable instructions may accessible via the network system 448. During operation, the processing member 458 can communicate with the sensor members 412, 444 to obtain data that reflects, respectively, the measured displacement and the operating temperature. The processing member 458 can utilize data stored locally, e.g., on the first memory 462, as well as external to the device 400, e.g., on the external server 456.

Figure 5:
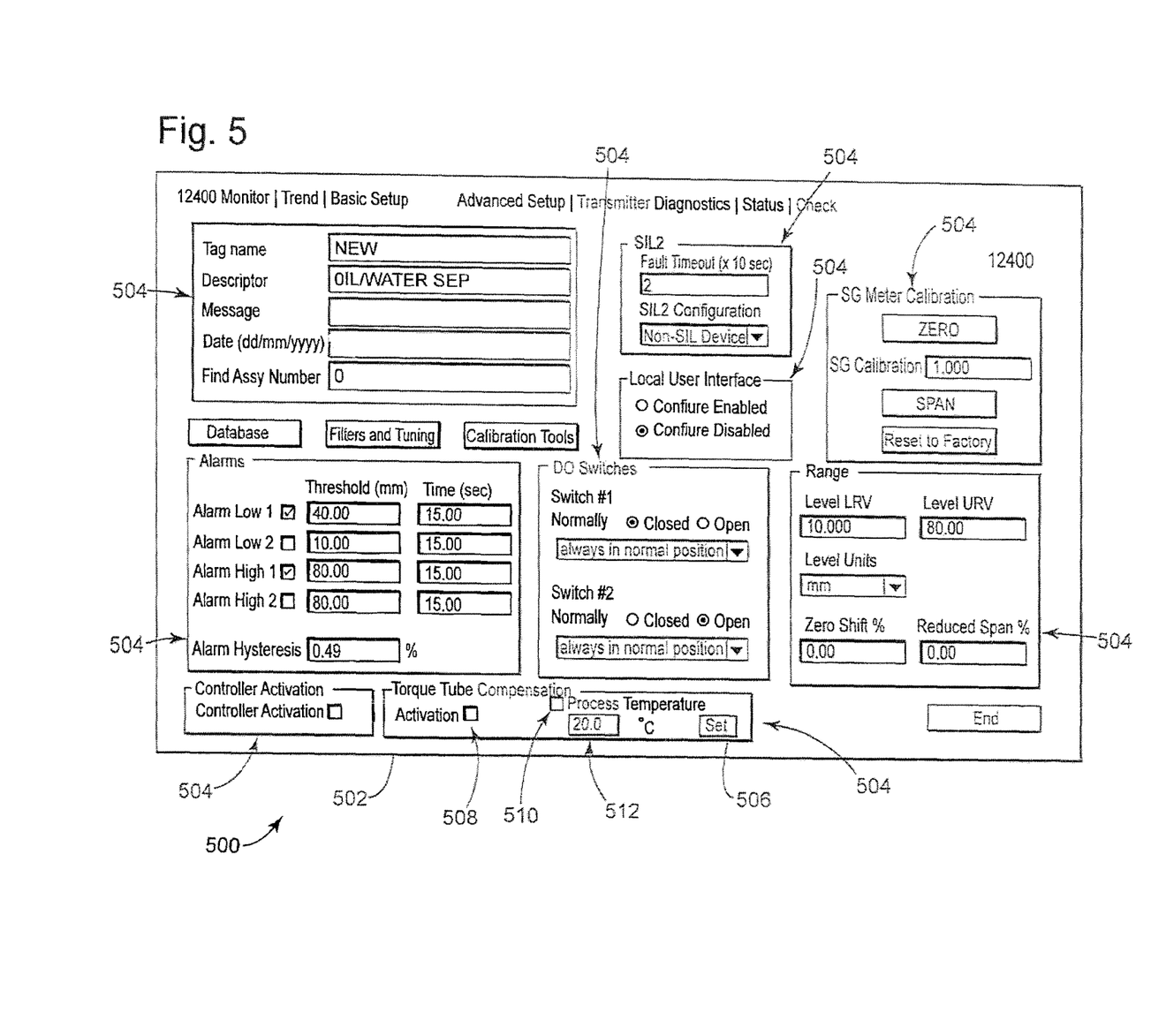
FIG. 5 depicts a screen shot of an example of an interface that can solicit information for use in the method of FIG. 1.

FIG. 5 depicts a screen shot of an example of an interface 500 that can solicit information for compensating for changes in operative characteristics in a liquid-level transmitter device. This example includes a user display 502 with one or more interface areas 504 that can display information that relate to operation of the liquid-level transmitter device. In one embodiment, the interface areas 504 can include a compensation area 506 with one or more selection icons (e.g., a first selection icon 508 and a second selection icon 510) and one or more input areas (e.g., a first input area 512).

Generally, the interface 500 can be part of a system-level control program for use by the process control system 446 (FIG. 4). These types of programs may reside on, for example, the process control server 452 (FIG. 4) for access by, e.g., the terminal 454 (FIG. 4). In this configuration, the terminal 454 (FIG. 4) may display the user display 502 for use by the end user.

Use of the user display 502 can facilitate compensation for changes in physical properties on the liquid-level transmitter device. The selection icons 508, 510 can solicit information from the end user, for example, that enables the compensation feature (e.g., by way of the first selection icon 508) and that identifies the appropriate operating mode (e.g., by way of the second selection icon 510). For the process mode, the input area 512 can receive information from the end user that indicate the process temperature for use in the compensation feature.

In light of the foregoing, the embodiments described herein are configured to compensate for changes in physical properties (and other operating characteristics) on liquid-level transmitter devices. These embodiments can use operating data, namely, data that reflects operating temperature on the interior of components of the devices. In this way, the embodiments forgo the need for additional, external sensors. Moreover, a technical effect of the configuration of these embodiments provides a built-in feature that improves accuracy of measured values by generating an output that compensates for the change, or drift, in the physical property automatically.

One or more of the steps of the methods (e.g., methods 100) can be coded as one or more executable instructions (e.g., hardware, firmware, software, software programs, etc.). These executable instructions can be part of a computer-implemented method and/or program, which can be executed by a processor and/or processing device. The processor may be configured to execute these executable instructions, as well as to process inputs and to generate outputs, as set forth herein. For example, the software can run and/or reside on the device and/or as software, application, or other aggregation of executable instructions on a separate computer, tablet, lap top, smart phone, and like computing device.

The computing components (e.g., memory and processor) can embody hardware that incorporates with other hardware (e.g., circuitry) to form a unitary and/or monolithic unit devised to execute computer programs and/or executable instructions (e.g., in the form of firmware and software). Exemplary circuits of this type include discrete elements such as resistors, transistors, diodes, switches, and capacitors. Examples of a processor include microprocessors and other logic devices such as field programmable gate arrays ("FPGAs") and application specific integrated circuits ("ASICs"). Memory includes volatile and non-volatile memory and can store executable instructions in the form of and/or including software (or firmware) instructions and configuration settings. Although all of the discrete elements, circuits, and devices function individually in a manner that is generally understood by those artisans that have ordinary skill in the electrical arts, it is their combination and integration into functional electrical groups and circuits that generally provide for the concepts that are disclosed and described herein.

Aspects of the present disclosure may be embodied as a system, method, or computer program product. The embodiments may take the form of an entirely hardware embodiment, an entirely software embodiment (including firmware, software, etc.) or an embodiment combining software and hardware aspects that may all generally be referred to herein as a "circuit," "module" or "system." The computer program may be embodied in one or more non-transitory computer readable medium(s) having computer readable program code embodied thereon.

Computer program code for carrying out operations for aspects of the present invention may be written in any combination of one or more programming languages, including an object oriented programming language and conventional procedural programming languages. Program code embodied on a computer readable medium may be transmitted using any appropriate medium, including but not limited to wireless, wireline, optical fiber cable, RF, etc., or any suitable combination of the foregoing.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of operating a liquid-level transmitter device, comprising:
    using a first sensor, measuring rotation of a torque tube that rotates in response to a level of liquid in a reservoir;
    using a second sensor, measuring operating temperature proximate the first sensor; and
    at a processing member, quantifying the level of liquid in the reservoir, the processing member having a processor with access to executable instructions, the executable instructions including one or more instructions for,
        receiving a first input that corresponds to the operating temperature;
        calculating a temperature deviation between the operating temperature and a calibrated temperature for the second sensor;
        defining a correction value using the temperature deviation and a drift value describing a %-change in Young's modulus of the torque tube relative to temperature; and
        generating an output defining a measured value that reflects the level of liquid in the reservoir, wherein the measured value incorporates the correction value to compensate for changes in the torque tube at the operating temperature.

2. The method of claim 1, wherein the correction value comprises a first correction value and a second correction value, which is different from the first correction value, and wherein each of the first correction value and the second correction value include a drift component that is calculated in accordance with, $$D = \frac{d_v * \Delta_t}{100}$$

in which D is the drift component, $d_v$ is the drift value, and $\Delta_t$ is the temperature deviation.

3. The method of claim 2, wherein the first correction value is calculated in accordance with, $$CV_1 = 1-D$$

in which $CV_1$ is the first correction value and D is the drift component, and wherein the second correction value is calculated in accordance with, $$CV_2 = D \times SG_{max} \times SG_{ratio},$$

in which $CV_2$ is the second correction value, D is the drift component, $SG_{max}$ is a first specific gravity value and $SG_{ratio}$ is a second specific gravity value that is different from the first specific gravity value.

4. The method of claim 3, wherein the output comprises a normalized value for the measured value, and wherein the normalized value is calculated in accordance with, $$L_N = (CV_1 \times M_N + CV_2),$$

in which $L_N$ is the normalized value, $CV_1$ is the first correction value, $CV_2$ is the second correction value, and $M_N$ is the measured value that is normalized between 0 and 1.

5. The method of claim 3, wherein the output comprises a current value for the measured value, and wherein the current value is calculated in accordance with, $$L_C = (CV_1 \times M_N + CV_3),$$

in which $L_C$ is the current value, $CV_1$ is the first correction value, $CV_2$ is the second correction value, and $CV_3$ is a third correction value, and wherein the third correction value is calculated in accordance with, $$CV_3 = M_{LZero} \times (CV_1 - 1) - (M_{LSpan} - M_{LZero}) \times CV_2,$$

in which $CV_3$ is the third correction value, $M_{LZero}$ is a low value for the measured value recorded from the a first sensor member during calibration, and $M_{LSpan}$ is a high value for the measured value recorded from the first sensor member during calibration.

6. An electronics component for use on a liquid-level transmitter device, said electronics component comprising:
    a housing forming an interior space;
    a first sensor member disposed in the interior space, the first sensor having components moveable relative to one another so as to generate a first signal that relates to a liquid level in a vessel;
    a second sensor member disposed in the interior space, the second sensor configured to generate a second signal that corresponds to operating temperature inside of the housing and proximate the first sensor member; and
    a processing member configured to couple with the first sensor member and the second sensor member, the processing member having a processor that is configured to access executable instructions stored on a memory and configured to be executed by the processor, the executable instructions comprising instructions for,
        receiving an input that corresponds to the operating temperature;
        calculating a temperature deviation between the operating temperature and a second input temperature;
        defining a correction value using the temperature deviation and a drift value stored locally in a data table, the data table comprising entries associating a %-change in Young's modulus for a material of a rotating shaft relative to temperature; and
        generating an output defining a measured value that reflects the level of liquid in the reservoir, wherein the measured value incorporates the correction value to compensate for changes in the component at the operating temperature.

7. The electronics component of claim 6, wherein the measured value includes a drift component that is calculated in accordance with, $$D = \frac{d_v * \Delta_t}{100}$$

wherein D is the drift component, $d_v$ is the drift value, and wherein $\Delta_t$ is a temperature deviation between a first input temperature and a second input temperature, at least one of which reflects data from the second sensor member.

8. The electronics component of claim 7, wherein the correction value comprises a first correction value and a second correction value, wherein the first correction value is calculated in accordance with, $$CV_1 = 1 - D$$

in which $CV_1$ is the first correction value and D is the drift component, and wherein the second correction value is calculated in accordance with, $$CV_2 = D \times SG_{max} \times SG_{ratio},$$

in which $CV_2$ is the second correction value, D is the drift component, $SG_{max}$ is a first specific gravity value and $SG_{ratio}$ is a second specific gravity value that is different from the first specific gravity value.

9. The electronics component of claim 8, wherein the output comprises a normalized value for the measured value, and wherein the normalized value is calculated in accordance with, $$L_N = (CV_1 \times M_N + CV_2),$$

in which $L_N$ is the normalized value, $CV_1$ is the first correction value, $CV_2$ is the second correction value, and $M_N$ is the measured value that is normalized between 0 and 1.

10. The electronics component of claim 8, wherein the output comprises a current value for the measured value, and wherein the current value is calculated in accordance with, $$L_C = (CV_1 \times M_N + CV_3),$$

in which $L_C$ is the current value, $CV_1$ is the first correction value, $CV_2$ is the second correction value, and $CV_3$ is a third correction value, and wherein the third correction value is calculated in accordance with, $$CV_3 = M_{LZero} \times (CV_1 - 1) - (M_{LSpan} - M_{LZero}) \times CV_2,$$

in which $CV_3$ is the third correction value, $M_{LZero}$ is a low value for the measured value recorded from the first sensor member during calibration, and $M_{LSpan}$ is a high value for the measured value recorded from the first sensor member during calibration.

* * * * *